(12) United States Patent
Park et al.

(10) Patent No.: US 12,239,722 B2
(45) Date of Patent: Mar. 4, 2025

(54) CAPSULE FOR COSMETICS

(71) Applicant: LG HOUSEHOLD & HEALTH CARE LTD., Seoul (KR)

(72) Inventors: No Jin Park, Seoul (KR); Byung Woo Hwang, Seoul (KR); Woo Sun Shim, Seoul (KR)

(73) Assignee: LG HOUSEHOLD & HEALTH CARE LTD., Seoul (KR)

(*) Notice: Subject to any disclaimer, the term of this patent is extended or adjusted under 35 U.S.C. 154(b) by 590 days.

(21) Appl. No.: 17/625,408

(22) PCT Filed: Jul. 8, 2020

(86) PCT No.: PCT/KR2020/008922
§ 371 (c)(1),
(2) Date: Jan. 7, 2022

(87) PCT Pub. No.: WO2021/006615
PCT Pub. Date: Jan. 14, 2021

(65) Prior Publication Data
US 2022/0273533 A1    Sep. 1, 2022

(30) Foreign Application Priority Data
Jul. 9, 2019  (KR) ........................ 10-2019-0082680

(51) Int. Cl.
| | | |
|---|---|---|
| *A61K 8/11* | (2006.01) | |
| *A61K 8/19* | (2006.01) | |
| *A61K 8/25* | (2006.01) | |
| *A61K 8/26* | (2006.01) | |
| *A61K 8/73* | (2006.01) | |
| *A61K 8/81* | (2006.01) | |
| *A61Q 19/00* | (2006.01) | |

(52) U.S. Cl.
CPC .................. *A61K 8/11* (2013.01); *A61K 8/19* (2013.01); *A61K 8/25* (2013.01); *A61K 8/26* (2013.01); *A61K 8/733* (2013.01); *A61K 8/8147* (2013.01); *A61Q 19/00* (2013.01); *A61K 2800/56* (2013.01)

(58) Field of Classification Search
CPC ... A61K 8/11; A61K 8/19; A61K 8/25; A61K 8/26; A61K 8/733; A61K 8/8147
See application file for complete search history.

(56) References Cited

U.S. PATENT DOCUMENTS

| | | |
|---|---|---|
| 2002/0064541 A1 | 5/2002 | Lapidot et al. |
| 2007/0149435 A1* | 6/2007 | Koenig .................. A61Q 17/00 442/121 |
| 2007/0149436 A1 | 6/2007 | Koenig et al. |
| 2011/0177951 A1 | 7/2011 | Toledano et al. |
| 2012/0202695 A1 | 8/2012 | Toledano et al. |
| 2017/0027823 A1 | 2/2017 | Weissbrodt et al. |

FOREIGN PATENT DOCUMENTS

| | | |
|---|---|---|
| CA | 2 093 431 C | 12/2002 |
| CN | 101810595 A | 8/2010 |
| CN | 107970227 A | 5/2018 |
| JP | 2011-523417 A | 8/2011 |
| KR | 10-2011-0084151 A | 7/2011 |
| KR | 10-2013-0008002 A | 1/2013 |
| KR | 10-2013-0031149 A | 3/2013 |
| KR | 10-2016-0063661 A | 6/2016 |
| WO | WO 2018/054351 A1 | 4/2016 |
| WO | WO 2017/165389 A2 | 9/2017 |

OTHER PUBLICATIONS

"Bio-Digestive Physiological Characteristics and Nutritional Design," Scientific Technical Literature Press, Jun. 2016, p. 264 (12 pages total), with an English translation.
Cao et al., "Application of Natural Biodegradable Polymer Wall Materials in Microcapsules," Materials Reports, vol. 37, No. 18, 2023, pp. 22010221-1 to 22010221-9, with an English abstract.
International Search Report, issued in PCT/KR2020/008922, mailed Oct. 20, 2020.

\* cited by examiner

*Primary Examiner* — Michael B. Pallay
(74) *Attorney, Agent, or Firm* — Birch, Stewart, Kolasch & Birch, LLP

(57) ABSTRACT

The present invention relates to a method for producing a capsule for cosmetics. The capsule for cosmetics produced according to the present invention has the advantage of being capable of stably storing an active ingredient and, unlike conventional technology, despite its large size, giving less texture upon rupturing.

12 Claims, 1 Drawing Sheet

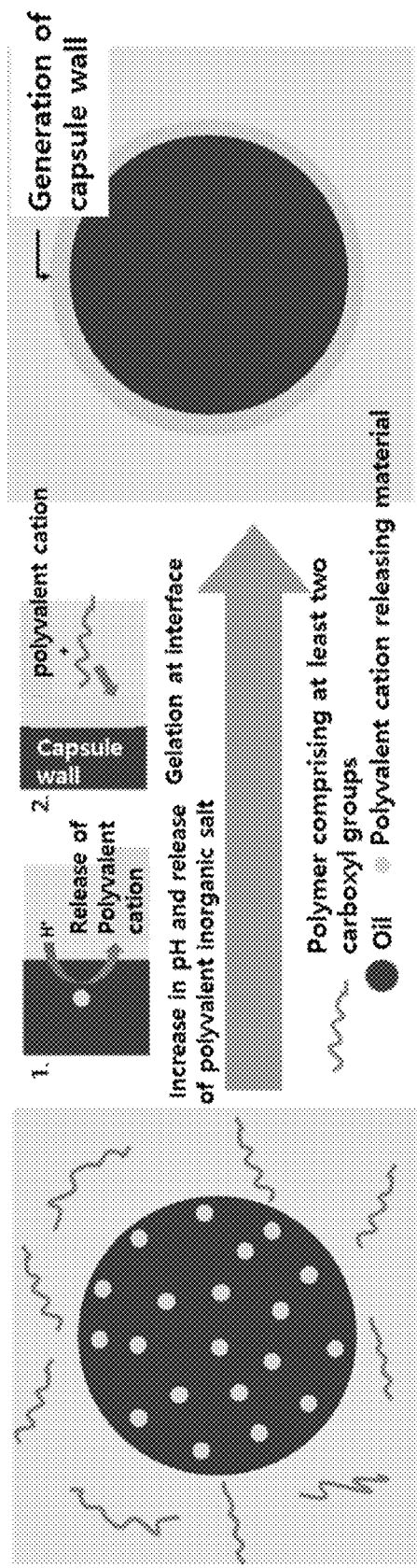

CAPSULE FOR COSMETICS

TECHNICAL FIELD

The present invention relates to a method for producing a capsule for cosmetics, and more particularly, to a capsule for cosmetics in which an active ingredient can be stably stored and unlike those of conventional technology, despite its large size, less texture is offered upon rupturing.

BACKGROUND ART

Encapsulation is known as a method utilized to solve problems related to an active ingredient losing its unique characteristics due to exposure to factors such as light and heat during storage of cosmetics and the like, or its activity deteriorating due to a decrease in concentration caused by physical phenomena such as evaporation. Encapsulation may enhance the stability of an active ingredient and may enable a user to activate the active ingredient at a desired time, and due to these benefits, it is used in many industrial fields. An example of a representative method for activating an encapsulated active ingredient includes a method of allowing the active ingredient to be gradually released or sustained by rupturing the outer wall of the capsule using factors such as pressure or inducing the formation of small holes in the outer wall of the capsule.

Although melamine-formaldehyde resin-based capsules are widely used commercially, there is a problem in that formaldehyde, which is a toxic material, must be present in the process of producing microcapsules. Therefore, there is increasing interest in a novel formaldehyde-free capsule.

Liposomal capsules, coacervation, microsponges and the like have been proposed as solutions to this problem. However, these methods exhibit limitations in that the stability of the capsule is reduced due to a use of a surfactant and an ionic component in a formulation and the ability to store the active ingredient deteriorating or the release of the active ingredient not being regulated. Therefore, these methods are not adequate with respect to replacing melamine capsules.

Capsules based on inorganic materials such as silica have been proposed as a new alternative, but there is a problem in that these capsules cannot be widely applied because the greater the amphipathicity of a core material, the more difficult it is to form an outer wall after a precursor, organopolysiloxane, moves to the interface. Further, the inorganic-material-based capsules have a disadvantage in that it is difficult to regulate the degree of activation of an active ingredient due to low elasticity and high hardness.

In contrast, organic-polymer-based capsules that are widely used in the industry, such as polyacryl-based, polyurea-based, and polyurethane-based capsules, have been considered as alternatives due to an advantage in that formaldehyde is not used, and they have a wide range of versatility and excellent economic feasibility. However, due to the high elasticity of the polymers themselves, it is hard to rupture these capsules by pressure, and therefore it is difficult to activate the active ingredient.

Furthermore, in addition to the aforementioned problems, the cosmetics industry is trying to produce capsules having a diameter of 100 µm or more in order to improve the aesthetic effect of the product and the visual satisfaction of consumers. However, when a general production method is used, there is a problem in that usage of an outer wall material is increased during the production of a capsule, which acts as giving texture when the capsule ruptures and results in low consumer satisfaction Therefore, there is a need for developing a capsule material for cosmetics that despite its large size, has a small amount of toxic materials high versatility and good economic feasibility, and exhibits a characteristic of giving less texture when the resulting capsule ruptures.

RELATED ART DOCUMENTS

Patent Document

1. Korean Patent Application Laid-Open No. 10-2011-0084151

DISCLOSURE

Technical Problem

To solve the aforementioned problem, an object of the present invention is to provide a capsule for cosmetics that despite its large size, has a small amount of toxic materials, high versatility and good economic feasibility, and exhibits a characteristic of giving less texture upon rupturing.

Technical Solution

The present invention provides a method for producing a capsule for cosmetics, the method including: preparing an emulsion by mixing a continuous phase including a polymer having at least two carboxyl groups and a dispersed phase including a polyvalent cation transporter; and adjusting the pH of the emulsion to 10 or less, followed by gelation.

Advantageous Effects

The present invention can provide a capsule for cosmetics that has a small amount of toxic materials, high versatility and good economic feasibility, and despite its large size, exhibits a characteristic of giving less texture upon rupturing.

Further, the present invention can provide an eco-friendly capsule for cosmetics because a natural polymer including at least two carboxyl groups is used as an outer wall material of the capsule.

DESCRIPTION OF DRAWINGS

The Figure is a schematic view illustrating a principle of producing the capsule for cosmetics according to the present invention.

MODES OF THE INVENTION

Hereinafter, the configuration of the present invention will be described in detail.

The present invention relates to a method for producing a capsule for cosmetics.

The present invention can produce a capsule for cosmetics that despite its large size, has a small amount of toxic materials, high versatility and good economic feasibility, and exhibits a characteristic of giving less texture upon rupturing.

The capsule for cosmetics can be produced by preparing an emulsion by mixing a continuous phase including a polymer having at least two carboxyl groups and a dispersed phase including a polyvalent cation transporter; and adjusting the pH of the emulsion to 10 or less, followed by gelation.

In an exemplary embodiment, the capsule for cosmetics according to the present invention can be produced by steps of preparing a continuous phase including a polymer having at least two carboxyl groups (hereinafter, Step 1);

preparing a dispersed phase including a polyvalent cation transporter (hereinafter, Step 2);

preparing an emulsion by mixing the continuous phase and the dispersed phase (hereinafter, Step 3); and adjusting the pH of the emulsion to 10 or less, followed by gelation (hereinafter, Step 4).

In the present invention, Step 1 involves preparing a continuous phase. The continuous phase is a material that is maintained in a liquid state at room temperature, and is at least one of the solvents generally used in such a process.

In the present invention, the continuous phase includes a polymer having at least two carboxyl groups. The polymer having at least two carboxyl groups may act as a material for forming an outer wall of a capsule produced in a gelation process to be described below. Specifically, the polymer having at least two carboxyl groups may enhance the dispersion stability of an emulsion formed by mixing the dispersed phase with the continuous phase at the interface of the emulsion, and may encounter cations in the gelation process that forms an outer wall through ionic bonds.

In an exemplary embodiment, the polymer having at least two carboxyl groups may include a compound represented by the following Chemical Formula 1.

[Chemical Formula 1]

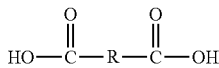

In Chemical Formula 1, R may include at least one selected from the group consisting of an alkylene having 1 to 50 carbon atoms and a cyclic hydrocarbon having 3 to 60 carbon atoms.

"Alkylene" refers to a saturated or unsaturated straight or branched chain hydrocarbon having a specified number of carbon atoms unless otherwise described. Further, "cyclic hydrocarbon" refers to a saturated or unsaturated cyclic hydrocarbon having the specified number of carbon atoms unless otherwise described. The cyclic hydrocarbon may include an aromatic compound.

In an exemplary embodiment, the alkylene having 1 to 50 carbon atoms or the cyclic hydrocarbon having 3 to 60 carbon atoms may or may not include at least one carboxyl group and/or at least one heteroatom In an exemplary embodiment, the alkylene having 1 to 50 carbon atoms may be specifically an alkylene having 1 to 30 carbon atoms, and the cyclic hydrocarbon having 3 to 60 carbon atoms may be specifically a saturated or unsaturated cyclic hydrocarbon (aromatic hydrocarbon) having 3 to 60 carbon atoms.

In an exemplary embodiment, the polymer of Chemical Formula 1 may include at least one selected from the group consisting of sodium alginate, sodium acrylate, sodium carbomer, sodium acrylate/C10-30 alkyl acrylate crosspolymer and sodium carboxymethyl cellulose.

In an exemplary embodiment, the polymer having at least two carboxyl groups may be included in an amount of 0.001 to 30 parts by weight, 0.01 to 10 parts by weight, 0.05 to 5 parts by weight or 0.1 to 1 parts by weight based on the total weight (100 parts by weight) of the continuous phase. When the content of the polymer having at least two carboxyl groups is less than 0.001 parts by weight, there is a concern that the emulsion may not be formed, and when the content exceeds 30 parts by weight, there is a concern of viscosity becoming too high. In addition, the polymer may be included in an amount of 0.001 to 100 parts by weight, 0.005 to 75 parts by weight, 0.01 to 50 parts by weight or 1 to 10 parts by weight based on the total weight (100 parts by weight) of the dispersed phase.

In an exemplary embodiment, the solvent of the continuous phase does not need to be particularly limited as long as the solvent can dissolve a polymer having at least two carboxyl groups, and in the present invention, water may be used as the solvent thereof.

In the present invention, Step 2 involves preparing a dispersed phase. The dispersed phase is a material that is maintained in a liquid state at room temperature, and is at least one of the solvents generally used in such a process.

In the present invention, the dispersed phase includes a polyvalent cation transporter. The polyvalent cation transport can release polyvalent cations at a pH of 10 or less in a gelation process to be described below. Specifically, the polyvalent cation transporter can be dispersed in the dispersed phase, and may react with the polymer having at least two carboxyl groups when the pH drops in the later steps to release polyvalent cations forming a capsule outer wall.

In an exemplary embodiment, the polyvalent cation is a cation with a charge of at least two, and can connect at least two carboxyl groups in which $H^+$ ions are dissociated. The polyvalent cation is an element with a charge of at least two during ionization, and may be selected from alkaline-earth metals, semimetals, transition metals, lanthanides and actinides, but is not limited thereto, and may be selected from $Mg^{2+}$, $Al^{3+}$, $Ca^{2+}$, $Zn^{2+}$, $Ba^{2+}$, $Sr^{2+}$, and the like.

In an exemplary embodiment, the polyvalent cation transporter is not limited thereto, but may be classified as a silicate compound, an oxide compound or a salt compound, which includes polyvalent cations.

A silicate compound is a compound including polyvalent cations, the element Si, and the element O in its chemical formula, The silicate compound can release polyvalent cations by an acid-base reaction or a redox reaction under a condition of pH 10 or less. As the silicate compound, it is possible to use at least one selected from the group consisting of aluminum calcium magnesium potassium sodium zinc silicate, aluminum calcium sodium silicate, aluminum iron calcium magnesium germanium silicate, aluminum iron calcium magnesium zirconium silicate, aluminum iron silicate, aluminum silicate, ammonium fluorosilicate, ammonium silver zinc aluminum silicate, calcium aluminum borosilicate, calcium magnesium silicate, calcium silicate, calcium sodium borosilicate, calcium sodium phosphosilicate, calcium titanium borosilicate, a C24-28 alkyldimethylsiloxy trimethylsiloxysilicate, lithium magnesium silicate, lithium magnesium sodium silicate, magnesium aluminometasilicate, magnesium aluminum silicate, magnesium fluorosilicate, magnesium potassium fluorosilicate, magnesium silicate, magnesium sodium fluorosilicate, magnesium trisilicate, silver borosilicate, sodium magnesium aluminum silicate, sodium magnesium fluorosilicate, sodium magnesium silicate, sodium potassium aluminum silicate, sodium silver aluminum silicate, tromethamine magnesium aluminum silicate, zinc borosilicate, zinc silicate, aluminum silicate, zirconium silicate, and the like.

An oxide compound is a compound including polyvalent cations and the element O in its chemical formula. The oxide compound can release polyvalent cations by an acid-base reaction or a redox reaction when the pH is 10 or less. As the oxide compound, it is possible to use at least one selected from the group consisting of aluminum/calcium/manganese oxide, barium/calcium/silicon/titanium oxide, calcium cerium oxide, calcium oxide, calcium peroxide, aluminum magnesium oxide, magnesium/manganese/titanium oxide, magnesium/potassium/silicon/fluoride/hydroxide/oxide, magnesium/potassium/titanium oxide, sodium phosphorus/zinc/calcium/silicon/aluminum/silver oxide, magnesium oxide and magnesium peroxide.

Furthermore, a salt compound is a material including polyvalent cations and anions in its chemical formula, where the anions form a complex with the polyvalent cations to make the net charge zero. The salt compound can release polyvalent cations by an acid-base reaction or dissociation under a condition of pH 10 or less. As a negative ion capable of being used as the salt compound, it is possible to use at least one selected from the group consisting of fluoride, chloride, bromide, iodide, sulfide, sulfate, carbonate, phosphate, hydroxide, pantothenate, acetate, alginate, ascorbate, aspartate, behenate, benzoate, carboxymethyl cellulose, carnaubate, carrageenan, caseinate, citrate, cyclamate, EDTA, DNA, dodecylbenzenesulfonate, ferrite, fructoborate, fructoheptonate, glucoheptonate, gluconate, glycerophosphate, glycinate, hydroxyapatite, hydroxymethionine, hypochlorite, ketogluconate, lactate, laurate, lauroyl taurate, lignosulfonate, monofluorophosphate, montanate, myristate, pantetheine sulfonate, pantothenate, paraben, PCA, phosphoryl oligosaccharides, polygamma-glutamate, polyglutamate, polyoxymethylene pyrrolidone, a carbomer, propionate, RNA, salicylate, beta-sitosteryl sulfate, a PVM/MA copolymer, sorbate, starch isododecenylsuccinate, starch octenylsuccinate, stearate, stearoyl lactylate, tartrate, thioglycolate, titanate, trifluoroacetate, undecylenate, xylenesulfonate, azelate, an acrylate copolymer, and the like.

In an exemplary embodiment, the polyvalent cation transporter may have a diameter of 1 nm to 500 μm, 1.5 nm to 250 μm, or 2 nm to 100 μm.

In an exemplary embodiment, the polyvalent cation transporter may be surface-treated with a surface treatment compound. In the present invention, uniform dispersion of the polyvalent cation transporter in the dispersion phase can be achieved by surface-treating it. In this case, as the surface treatment compound, it is possible to use a non-covalent surface treatment compound such as cetyltrimethylammonium bromide, cetyltrimethylammonium chloride, disteardimonium chloride or aluminum stearate; or a covalent surface treatment compound such as a halosilane-based compound or an alkoxysilane.

In an exemplary embodiment, the content of the polyvalent cation transporter may be 0.002 to 30 parts by weight, 0.006 to 25 parts by weight, or 0.011 to 20 parts by weight based on the total weight (100 parts by weight) of the dispersed phase. When the content of the polyvalent cation transporter is less than 0.002 part by weight, there is a concern that the capsule may not be formed, and when the content exceeds 30 parts by weight, there is a concern that a capsule with texture upon rupturing may be formed due to a quick reaction thereof.

In an exemplary embodiment, the solvent of the dispersed phase is not particularly limited as long as the solvent is immiscible with the continuous phase. When water is used as the solvent of the continuous phase, as the solvent of the dispersed phase, it is possible to use at least one selected from the group consisting of a hydrocarbon-based solvent; a solvent including an ether group; a solvent including an ester group; a solvent including a ketone group; a solvent including benzene; a haloalkane-based solvent; and a silicone-based solvent.

The hydrocarbon-based solvent may be selected from compounds having a linear or non-linear structure, such as pentane, hexane, cyclohexane, heptane, octane, isododecane and dodecane, the solvent including an ether group may be selected from ethyl ether, butyl ether and methyl-t-butyl ether, and the solvent including an ester group may be selected from ethyl acetate, butyl actetate and ethyl butyrate. Further, the solvent including a ketone group may be methyl ethyl ketone, the solvent including benzene may be selected from benzene, toluene and xylene, the haloalkane-based solvent may be selected from dichrolomethane, dichloroethane, chloroform and carbon tetrachloride, and the silicone-based solvent may be selected from dimethicone and cyclomethicone.

In an exemplary embodiment, the dispersed phase of the present invention may further include an active ingredient in addition to the above-described polyvalent cation transporter. The active ingredient is a material whose activity is desired to be maintained by the resulting capsule, and the activity of the active ingredient may be exhibited upon the rupture of the outer wall of the capsule in later steps. When the active ingredient is a liquid at room temperature, the active ingredient may replace the dispersed phase, which is the solvent, and otherwise the use of active ingredient may vary depending on its solubility. As the solvent, it is possible to use at least one selected from the group consisting of a fragrance, a dye, a catalyst, an antioxidant, a drug, and the like.

In the present invention, Step 3 involves forming an emulsion by mixing the above-described continuous phase and dispersed phase.

In an exemplary embodiment, the content of the dispersed phase may be 1 to 90 parts by weight, 2 to 85 parts by weight, or 3 to 80 parts by weight based on the mixed weight (100 parts by weight) of the dispersed phase and the continuous phase.

In an exemplary embodiment, this step may be performed by adding the dispersed phase to the continuous phase, and may be performed by stirring the mixture.

In an exemplary embodiment, the stirring may be performed at 1 to 16000 RPM, 5 to 13000 RPM, or 10 to 10000 RPM at 20 to 30° C., or room temperature.

In an exemplary embodiment, the step may be performed at a pH of 7 to 12.

In an exemplary embodiment, the size of the prepared emulsion may be 100 μm or more.

In the present invention, Step 4 involves adjusting the pH of the emulsion to 10 or less, followed by gelation.

A capsule for cosmetics may be produced through this step. Specifically, as illustrated in the Figure, the capsule is formed at an interface formed after the continuous phase and the dispersed phase are mixed. At the interface, the outer wall of the capsule may be formed by reacting (gelling) a polymer having at least two carboxyl groups with polyvalent cations released from the polyvalent cation transporter. In the present invention, the texture upon the rupture of the capsule may be alleviated by adjusting the rate of gelation.

In an exemplary embodiment, under the condition of a pH of 10 or less, the polyvalent cation transport releases polyvalent cations, and the released polyvalent cations and the polymer having at least two carboxyl groups may form a capsule for cosmetics that has a small amount of toxic materials and shows high versatility and good economic feasibility as a result of slowly performing gelation at the interface. In particular, in the present invention, since polyvalent cations are slowly released due to a drop in the pH of the continuous phase and the gelation process, an outer wall which has low hardness but is capable of stabilizing the interface may be formed, and a capsule giving less texture upon rupturing may be produced.

In an exemplary embodiment, this step may be performed at a pH of 10 or less, 1 to 10, 2 to 9, or 3 to 8. In addition, the time interval between the forming of the emulsion, which is Step 3, and the drop in pH for forming the outer wall of the capsule may be 1 to 120 minutes, 2 to 90 minutes, or 3 to 60 minutes.

In an exemplary embodiment, the gelation for producing the capsule may be performed at 0 to 100° C. for 1 to 1440 minutes, at 10 to 90° C. for 2 to 720 minutes, and at 20 to 80° C. for 3 to 360 minutes.

In an exemplary embodiment, the gelation may be performed by stirring, and the stirring may be performed at 1 to 6000 RPM, 5 to 5000 RPM, or 10 to 4000 RPM.

Under the above conditions, polyvalent cations may be released at the interface between the continuous phase and the dispersed phase as the pH drops, and an outer wall may be formed by gelation.

In an exemplary embodiment, the gelation may be performed in the presence of a dispersion stabilizer. The dispersion stabilizer may be used for the purpose of enhancing the dispersibility of the capsule produced after the reaction, As the dispersion stabilizer, it is possible to use at least one selected from the group consisting of gum arabic, polysaccharides, pectin, alginate, arabinogalactan, carrageenan, gellan gum, xanthan gum, guar gum, acrylate/acrylic polymers, starch, water-swellable clay, acrylatelate/aminoacrylate copolymers, and a mixture thereof; maltodextrin; a natural gum such as alginate ester; gelatin, protein hydrolysates, and a quaternized form thereof; and synthetic polymers and copolymers such as poly(vinyl pyrrolidone-co-vinyl acetate), poly(vinyl alcohol-co-vinyl acetate), poly(maleic acid), poly(alkylene oxides), poly(vinylmethyl ether), poly(vinyl ether-co-maleic anhydride), poly(ethyleneimine), poly((meth)acrylamide), poly(alkyleneoxide-co-dimethylsiloxanes), poly(aminodimethylsiloxane), and the like.

The present invention may further include curing the outer wall of the formed capsule after performing gelation. In this case, the time for curing may be 5 minutes to 48 hours, 7 minutes to 36 hours, or 10 minutes to 24 hours.

In the present invention, a step of concentrating and/or drying the produced capsule for cosmetics may be further performed, if necessary.

Furthermore, the pH may be adjusted by using an acid or a basic material, but the conditions thereof are not limited. Further, in the process, a process of dissolving a preservative, a moisturizer, a whitening effect component, a wrinkle reducing component, and the like that are required for cosmetics in an external phase and introducing the required components may be performed, and the conditions thereof are not limited.

In addition, the present invention relates to a capsule for cosmetics that is produced by the above-described method for producing a capsule for cosmetics.

The capsule for cosmetics according to the present invention may have a diameter of 10 μm to 10,000 μm, 50 to 5,000 μm, or 100 to 1000 μm.

Furthermore, the capsule may have a wall thickness of 0.05 to 100 μm.

Hereinafter, the present invention will be described in detail with reference to the examples. However, the following examples are only for the purpose of exemplifying the present invention, and the scope of the present invention is not limited to the following examples. The present examples are provided to make the disclosure of the present invention complete and to allow a person skilled in the art to which the present invention belongs to completely comprehend the scope of the present invention, and the present invention is defined only by the scope of the claims.

EXAMPLES

Examples 1 to 11. Production of Capsule to Which Polymer Having at least Two Carboxyl Groups and Polyvalent Cation Transporter is Applied Capsules for cosmetics were produced using the components in Tables 1 and 2 and the following method.

Step 1: a continuous phase was prepared by dispersing a polymer having at least two carboxyl groups in 89.8 g of distilled water.

Step 2: a dispersed phase was prepared by putting 0.1 g of a polyvalent cation transporter into 9.9 g of dodecane.

Step 3: an emulsion was prepared by slowly putting the dispersed phase into the continuous phase while stirring at 50 RPM. Then, after the pH was lowered to 10 or less, capsules for cosmetics were produced by performing gelation for 30 minutes.

Comparative Example 1

A capsule for cosmetics was produced using the components in Table 1 and the following method.

Step 1: a continuous phase was produced by putting sodium alginate into 80 g of distilled water.

Step 2: 9.9 g of dodecane, which is a dispersed phase, was prepared.

Step 3: an emulsion was prepared by slowly putting the dispersed phase into the continuous phase while stirring at 50 RPM. Then, after a solution of calcium chloride ($CaCl_2$) dissolved in 9 g of distilled water was added to the emulsion, a capsule for cosmetics was produced by performing gelation for 30 minutes.

Comparative Example 2

A capsule for cosmetics was produced using the components in Table 1 and the following method.

Step 1: a continuous phase was prepared by putting sodium alginate into 89.8 g of distilled water.

Step 2: 9.9 g of dodecane, which is a dispersed phase, was prepared.

Step 3: an emulsion was prepared by slowly putting the dispersed phase into the continuous phase while stirring at 50 RPM. Then, after magnesium aluminum silicate was added thereto, a capsule for cosmetics was produced by lowering the pH to 10 or less, and subsequently performing gelation for 30 minutes.

TABLE 1

|  |  | Comparative Example 1 | Comparative Example 2 | Example 1 | Example 2 | Example 3 | Example 4 | Example 5 |
|---|---|---|---|---|---|---|---|---|
|  | Distilled water | 89 | 89.8 | 89.8 | 89.8 | 89.8 | 89.8 | 89.8 |
| Polyvalent cation transporter | Magnesium aluminum silicate | — | 0.1 | 0.1 | 0.1 | 0.1 | 0.1 | 0.1 |
|  | Aluminum calcium sodium silicate | — | — | — | — | — | — | — |
|  | Magnesium potassium fluorosilicate | — | — | — | — | — | — | — |
|  | Magnesium sodium fluorosilicate | — | — | — | — | — | — | — |
|  | Sodium magnesium aluminum silicate | — | — | — | — | — | — | — |
|  | Lithium magnesium sodium silicate | — | — | — | — | — | — | — |
|  | Calcium oxide | — | — | — | — | — | — | — |
|  | $CaCO_3$ | — | — | — | — | — | — | — |
|  | $CaCl_2$ | 0.1 | — | — | — | — | — | — |
| Polymer having at least two carboxyl groups | Sodium alginate | 1 | 0.2 | 0.2 | — | — | — | — |
|  | Sodium acrylate | — | — | — | 0.2 | — | — | — |
|  | Sodium carbomer | — | — | — | — | 0.2 | — | — |
|  | Sodium Acrylate/C10-30 alkyl-acrylate crosspolymer | — | — | — | — | — | 0.2 | — |
|  | Sodium carboxymethyl cellulose | — | — | — | — | — | — | 0.2 |
|  | Dodecane | 9.9 | 9.9 | 9.9 | 9.9 | 9.9 | 9.9 | 9.9 |

TABLE 2

|  |  | Example 6 | Example 7 | Example 8 | Example 9 | Example 10 | Example 11 |
|---|---|---|---|---|---|---|---|
|  | Distilled water | 89.8 | 89.8 | 89.8 | 89.8 | 89.8 | 89.8 |
| Polyvalent cation transporter | Aluminum calcium sodium silicate | 0.1 | — | — | — | — | — |
|  | Magnesium potassium fluorosilicate | — | 0.1 | — | — | — | — |
|  | Magnesium sodium fluorosilicate | — | — | 0.1 | — | — | — |
|  | Sodium magnesium aluminum silicate | — | — | — | 0.1 | — | — |
|  | Lithium magnesium sodium silicate | — | — | — | — | 0.1 | — |
|  | Calcium Oxide | — | — | — | — | — | 0.1 |
|  | $CaCO_3$ | — | — | — | — | — | — |

TABLE 2-continued

|  |  | Example 6 | Example 7 | Example 8 | Example 9 | Example 10 | Example 11 |
|---|---|---|---|---|---|---|---|
| Polymer having at least two carboxyl groups | Sodium alginate | 0.2 | 0.2 | 0.2 | 0.2 | 0.2 | 0.2 |
| | Sodium acrylate | — | — | — | — | — | — |
| | Sodium carbomer | — | — | — | — | — | — |
| | Sodium acrylate/ C10-30 alkyl acrylate crosspolymer | — | — | — | — | — | — |
| | Sodium carboxymethyl cellulose | — | — | — | — | — | — |
| Dodecane | | 9.9 | 9.9 | 9.9 | 9.9 | 9.9 | 9.9 |

Experimental Example 1. Comparison of Sizes and Texture Upon Rupturing of Capsules for Cosmetics For the capsules for cosmetics produced in Examples 1 to 11 and Comparative Examples 1 and 2, sizes, texture upon rupturing and stability were measured.

The capsule sizes were measured using Mastersizer 3000 manufactured by Malvern instruments Ltd. For texture upon rupturing, 20 skilled panelists performed a sensory evaluation on a scale of 1 point for "lowest texture upon rupturing" to 10 points for "highest texture upon rupturing," and then the resulting points were averaged to compare the texture upon rupturing for each production method. Further, stability was compared by measuring the change in size and quantifying the oil in the capsule (using LC-MS) before and after storing the capsules at 40° C. for 1 month.

The measurement results are shown in Tables 3 and 4.

TABLE 3

|  | Comparative Example 1 | Comparative Example 2 | Example 1 | Example 2 | Example 3 | Example 4 | Example 5 |
|---|---|---|---|---|---|---|---|
| Size (μm) | 31 | — | 145 | 107 | 114 | 133 | 122 |
| Texture upon rupturing (points) | 8.72 | — | 1.31 | 1.5 | 1.72 | 1.22 | 1.89 |
| Decrease in size after 1 month at 40° C. (%) | — | — | 0.5 | 0.5 | 0.5 | 0.5 | 0.5 |
| Amount of oil remaining after 1 month at 40° C. (%) | — | — | 99 | 99 | 99 | 99 | 99 |

TABLE 4

|  | Example 6 | Example 7 | Example 8 | Example 9 | Example 10 | Example 11 |
|---|---|---|---|---|---|---|
| Size (μm) | 145 | 156 | 138 | 149 | 150 | 141 |
| Texture upon rupturing (points) | 2.4 | 1.49 | 2.14 | 1.38 | 1.64 | 1.17 |
| Decrease in size after 1 month at 40° C. (%) | 0.5 | 0.5 | 0.5 | 0.5 | 0.5 | 0.5 |
| Amount of oil remaining after 1 month at 40° C. (%) | 99 | 99 | 99 | 99 | 99 | 99 |

As shown in Tables 3 and 4, the capsule of Comparative Example 1, which was produced by a general capsule production method, exhibited texture upon rupturing, and a capsule having a small size was produced. In addition, in Comparative Example 2, no capsule was produced.

In Examples 1 to 11, capsules having a size of 100 μm or more were produced. The capsules of the Examples showed a lower texture upon rupturing than Comparative Example 1, which was produced by a general production method. Furthermore, it can be confirmed that high stability was exhibited because the amount of change in size and in oil was small during a period of long-term storage.

INDUSTRIAL APPLICABILITY

The present invention can provide a capsule for cosmetics that despite its large size, has a small amount of toxic materials, high versatility and good economic feasibility, and exhibits a characteristic of giving less texture upon rupturing.

The invention claimed is:

1. A method for producing a capsule for cosmetics, the method comprising:
preparing an emulsion by mixing a continuous phase comprising a polymer having at least two carboxyl groups and a dispersed phase comprising a polyvalent cation transporter; and
adjusting the pH of the emulsion to 10 or less, followed by gelation,
wherein the step of adjusting the pH of the emulsion to 10 or less is performed in a range of 1 minute to 120 minutes after the emulsion is prepared.

2. The method of claim 1, wherein the polymer having at least two carboxyl groups is a compound represented by the following Chemical Formula 1:

[Chemical Formula 1]

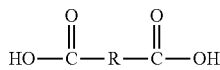

in Chemical Formula 1, R comprises at least one selected from the group consisting of an alkylene having 1 to 50 carbon atoms and a cyclic hydrocarbon having 3 to 60 carbon atoms.

3. The method of claim 1, wherein a content of the polymer having at least two carboxyl groups is 0.001 to 30 parts by weight with respect to a total weight of the continuous phase of 100 parts by weight.

4. The method of claim 1, wherein a solvent of the continuous phase is water.

5. The method of claim 1, wherein the polyvalent cation transporter is a compound which releases polyvalent cations at a pH of 10 or less.

6. The method of claim 5, wherein the polyvalent cation transporter comprises at least one selected from the group consisting of a silicate compound, an oxide compound and a salt compound, which comprise polyvalent cations.

7. The method of claim 1, wherein a content of the polyvalent cation transporter is 0.002 to 30 parts by weight with respect to a total weight of the dispersed phase of 100 parts by weight.

8. The method of claim 1, wherein a solvent of the dispersed phase comprises at least one selected from the group consisting of a hydrocarbon-based solvent; a solvent comprising an ether group; a solvent comprising an ester group; a solvent comprising a ketone group; a solvent comprising benzene; a haloalkane-based solvent; and a silicone-based solvent.

9. The method of claim 1, wherein the dispersed phase further comprises an active ingredient, wherein the active ingredient comprises at least one selected from the group consisting of a fragrance, a dye, a catalyst, an antioxidant and a drug.

10. The method of claim 1, wherein the preparation of the emulsion is performed under a condition of 1 to 16000 RPM.

11. The method of claim 1, wherein the gelation is performed under conditions of 0 to 100° C., 1 to 1440 minutes and 1 to 6000 RPM.

12. A capsule for cosmetics prepared by the method of claim 1, wherein the capsule has a diameter of 10 to 10,000 μm and a wall thickness of 0.05 to 100 μm.

* * * * *